(12) United States Patent
Atwood

(10) Patent No.: US 7,105,703 B1
(45) Date of Patent: Sep. 12, 2006

(54) CLEAVAGE OF PHOSPHATE ESTER BONDS BY USE OF NOVEL GROUP 13 CHELATE COMPOUNDS

(75) Inventor: David A. Atwood, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 11/166,936

(22) Filed: Jun. 23, 2005

(51) Int. Cl.
*C07F 9/02* (2006.01)
*C07F 5/00* (2006.01)
*B01J 31/00* (2006.01)

(52) U.S. Cl. ............................ 568/8; 556/32; 502/167
(58) Field of Classification Search ................ 556/32; 568/8; 502/167
See application file for complete search history.

(56) References Cited

U.S. PATENT DOCUMENTS

| | | | |
|---|---|---|---|
| 3,895,041 | A | 7/1975 | Inman et al. |
| 4,555,559 | A | 11/1985 | Kimura et al. |
| 4,576,647 | A | 3/1986 | Matsushita |
| 4,842,734 | A | 6/1989 | Wright et al. |
| 5,763,172 | A | 6/1998 | Magda et al. |
| 5,798,491 | A | 8/1998 | Magda et al. |
| 6,410,664 | B1 | 6/2002 | Bansleben et al. |
| 6,576,779 | B1 | 6/2003 | Bansleben et al. |
| 2003/0105250 | A1 | 6/2003 | Whiteker |

OTHER PUBLICATIONS

Munoz-Hernandez et al., Reactivity and Derivatization of Five-Coordinate, Chelated Aluminum, Inorganic Chemistry, vol. 40, No. 26, pp. 6782-6787 (Nov. 10, 2001).*
Wang et al., Ligand-Tetrahydrofuran Coupling in Chelated Aluminum Phosphinates, Inorganic Chemistry, vol. 41, No. 3, pp. 558-565 (Jan. 5, 2002).*
Wang et al., Five-coordinate organnoaluminum acetylides and crystal structure of the Iydrosylate, [Salophen(tBu)Al]2O, Journal of Organometallic Chemistry, vol. 689, pp. 759-765 (Feb. 16, 2004).*
David, Michael D. et al., Accelerated hydrolysis of industrial organophosphates in water and soil using sodium perborate; Environ. Pollution 105 (1999) 121-128.
Olivanen, Mikko et al., Kinetics and Mechanisms for the Cleavage and Isomerization of the Phosphodiester Bonds of RNA by Bronsted Acids and Bases; Chem. Rev. 1998, 98, 961-990.
Blasko, Andrei et al., Recent Studies of Nucleophilic, General-Acid, and Metal Ion Catalysis of Phosphate Diester Hydrolysis; Acc. Chem. Res. 1999, 32, 475-484.
Bazzicalupi, Carla et al., Carboxy and Diphosphate Ester Hydrolysis by a Dizinc Complex with a New Alcohol-Pendant Macrocycle; Inorg. Chem. 1999, 38, 4115-4122.
Gajda, Tamas et al., Highly Efficient Phosphodiester Hydrolysis Promoted by a Dinuclear Copper (II) Complex; Inorg. Chem., 2001, 40, 4918-4927.
Jones, David R. et al., Enhanced Base Hydrolysis of Coordinated Phosphate Esters: The Reactivity of an Unusual Cobalt (III) Amine Dimer; J. Am. Chem. Soc. 1984, 106, 7807-7819.
Vance, David H. et al., Functional Group Convergency in a Binuclear Dephosphorylation Reagent; J. Am. Chem. Soc., 1993, 115, 12165-12166.
McCue, Kevin P. et al., Hydrolysis of a Model for the 5'-Cap of mRNA by Dinuclear Copper (II) and Zinc (II) Complexes . . . Rapid Hydrolysis by Four Copper (II) Ions; Inorg. Chem. 1999, 38, 6136-6142.
Scrimin, Paolo et al., Comparative Reactivities of Phosphate Ester Cleavages by Metallomicelles, Langmuir 1996, 12, 6235-6241.
Kaminskaia, Natalia V., et al., Reactivity of u-Hydroxodizinc (II) Centers in Enzymatic Catalysts through Model Studies; Inorg. Chem. 2000, 39, 3365-3373.
Yamami, Masako et al., Macrocyclic Heterodinuclear ZnIIPbII Complexes: Synthesis, Structures and Hydrolytic Function toward Tris(p-nitrophenyl) Phosphate; Inorg. Chem. 1998, 37, 6832-6838.
Chapman, William H. Jr. et al., Selective Hydrolysis of Phosphate Esters, Nitrophenyl Phosphates and UpU, by Dimeric Zinc Complexes Depends on the Spacer Length; J. Am. Chem. Soc. 1995, 117, 5462-5469.
Molenveld, Peter et al., Highly Efficient Phosphate Diester Transesterification by a Calix[4]arene-Based Dinuclear Zinc(II) Catalyst;J. Am. Chem. Soc. 1997, 119, 2948-2949.
Benton, F.L. et al., The Cleavage of Ethers with Boron Bromide; Contrib. from Chemical Labs of U. of Notre Dame, May 1942; vol. 64 p. 1128.
Kim, Sunggak et al., Direct Conversion of Silyl Ethers into Alkyl Bromides with Boron Tribromide, J. Org. Chem. 1988, 53, 3111-3113.
Wei, Pingrong et al., Synthesis and Structure of Salen-Supported Borates Containing Siloxides, Inorg. Chem. 1999, 38, 3914-3918.
Brown, David S., An Intramolecularly Stabilized Arylboron Dibromide, Heteroatom Chem. vol. 9, No. 1, 1998, 79-83.
Yang, Yu-Chu, Chemical Detoxification of Nerve Agent VX, Acc. Chem. Res. 1999, 32, 109-115.
Ember, Lois, Destroying chemical arms: No easy task, C&EN Aug. 30, 1999, 11.
Hileman, Bette, EPA Cuts Use of Common Pesticide, C&EN Jun. 12, 2000, 11.
Goodman, Steven N. et al., A Practical Synthesis of a,B-Unsaturated Imides, Useful Substrates For Asymmetric Conjugate Addition Reactions, Adv. Synth. Catal. 2002, 344, No. 9.

* cited by examiner

*Primary Examiner*—Porfirio Nazario-Gonzalez
(74) *Attorney, Agent, or Firm*—King & Schickli, PLLC

(57) ABSTRACT

A novel chemical compound has a general formula $(LX)_nY$ wherein X is selected from a group consisting of a group 13 element other than boron, Y is selected from a group consisting of a halide, a chlorate, a sulfate and a nitrate and L is a chelating ligand containing two nitrogen and two oxygen donor groups where n=1 or 2.

6 Claims, No Drawings

CLEAVAGE OF PHOSPHATE ESTER BONDS BY USE OF NOVEL GROUP 13 CHELATE COMPOUNDS

TECHNICAL FIELD

The present invention relates generally to novel compounds, compositions and methods for the cleavage of phosphate ester bonds.

BACKGROUND OF THE INVENTION

Chemical warfare agents such as Sarin gas and VX and pesticides/insecticides such as chloropyrifos, paraoxon and parathion exhibit extreme toxicity. Each of these compounds includes a phosphate ester bond. Such compounds irreversibly block a serine hydroxy group in the cellular enzyme acetylcholinesterase by phosphorylation, thereby disrupting a cell's neurological function.

The safe destruction of such compounds is of great environmental concern. Accordingly, substantial effort has been devoted to development of methods for decontamination of such nerve agents, pesticides and insecticides. Toward that end, the cleavage of the P—O—C bond in these compounds has been targeted as a method of decontamination. Many such methods use d-block metals such as cobalt, copper, and zinc. It is also known to destroy nerve agents by hydrolyzing them using basic solutions and/or bleach to oxidize them to less toxic inorganic phosphates and alkali. However, these solutions are caustic and should only be handled under carefully controlled conditions. Large excesses of bleach and/or bases are required for successful decontamination, and the active agent (chlorine) in bleach decreases with time. Bases and bleach are also not selective for nerve agents, and readily undergo undesirable and potentially explosive side reactions. In addition, bleach is corrosive to surfaces of many materials it contacts.

There is accordingly identified a need in the art for a successful deactivating/destroying agent for such toxic nerve agents as nerve gas (Sarin gas, VX, and the like) and organophosphate pesticides. Such an agent should (a) be easily synthesized from inexpensive reagents, (b) be soluble in the same solvents as the nerve gases/pesticides, (c) be selective for the nerve agents, (d) not readily undergo unwanted side effects upon reaction with the nerve agents, and (e) be substantially non-toxic. Significantly, such a deactivating/destroying agent will also be useful in deactivating or destroying other organic or biological agents that include phosphate ester bonds.

SUMMARY OF THE INVENTION

In accordance with the purposes of the present invention as described herein, a novel compound is provided comprising

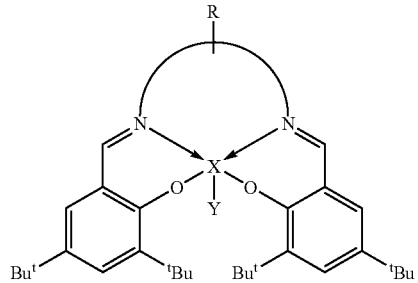

wherein R=alkyl, aryl or alkylaryl, X=a group 13 element other than boron and Y=a potential counteranion.

Alternatively, the novel compound may be described as comprising

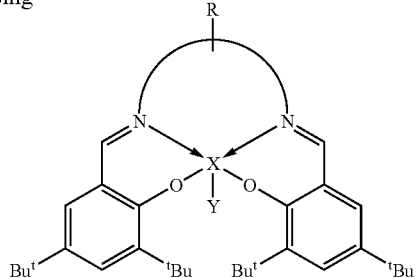

wherein R=—(CH$_2$)$_2$—, —(CH$_2$)$_3$— and a phenyl group, X=aluminum, gallium, indium or thallium and Y=a halide, a chlorate or a nitrate.

In yet another alternative the compound of the present invention may be described as comprising a general formula (LX)$_n$Y wherein X is selected from a group consisting of aluminum, gallium, indium and thallium; Y is selected from a group consisting of a halide, a chlorate, a sulfate and a nitrate; and L is a chelating ligand containing two nitrogen and two oxygen donor groups where n=1 or 2. The ligand framework provides two covalent oxygen atoms and two coordinate covalent nitrogen atoms. There are many ways in which such a coordinate environment can be provided. Salen ligands are readily illustrative of a simple, inexpensive means of providing such an environment.

In accordance with yet another aspect of the present invention a composition is provided for cleaving phosphate ester bonds. The composition comprises an effective amount of an active agent selected from a group of compounds consisting of

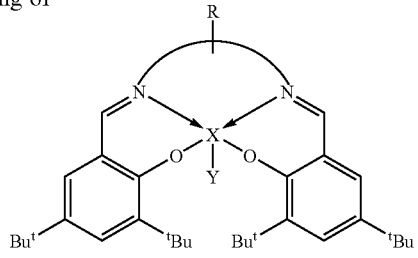

wherein R=alkyl, aryl or alkylaryl, X=a group 13 element other than boron and Y=a counteranion and a compatible solvent.

Alternatively the composition for cleaving phosphate ester bonds may be described as comprising an effective amount of an active agent selected from a group of compounds consisting of

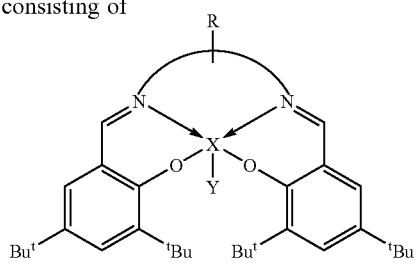

wherein R=—(CH$_2$)$_2$—, —(CH$_2$)$_3$— and a phenyl group, X=aluminum, gallium, indium or thallium and Y=a halide, a chlorate or a nitrate and a compatible solvent.

In still another alternative, the composition for cleaving phosphate ester bonds may be described as comprising an effective amount of an active agent selected from a group of compounds consisting of a general formula $(LX)_nY$ wherein X is selected from a group consisting of aluminum, gallium, indium and thallium; Y is selected from a group consisting of a halide, a chlorate, a sulfate and a nitrate; and L is a chelating ligand containing two nitrogen and two oxygen donor groups where n=1 or 2; and a compatible solvent.

In accordance with yet another aspect of the present invention, a method is provided for cleaving a phosphate ester bond. The method comprises reacting a phosphate ester bond containing compound with an active agent selected from a group of compounds consisting of

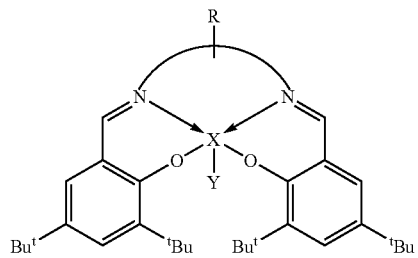

wherein R=alkyl, aryl or alkylaryl, X=a group 13 element other than boron and Y=a potential counteranion.

Alternatively, the method may be described as comprising the step of reacting a phosphate ester bond containing compound with an active agent selected from a group of compounds consisting of

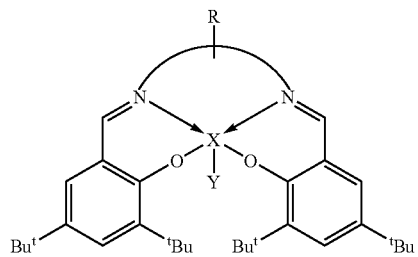

wherein R=—$(CH_2)_2$—, —$(CH_2)_3$— and a phenyl group, X=aluminum, gallium, indium or thallium and Y=a halide, a chlorate or a nitrate.

Still further the method for cleaving a phosphate ester bond may be alternatively described as comprising reacting a phosphate ester bond containing compound with an active agent selected from a group of compounds consisting of a general formula $(LX)_nY$ wherein X is selected from a group consisting of aluminum, gallium, indium and thallium; Y is selected from a group consisting of a halide, a chlorate, a sulfate and a nitrate; and L is a chelating ligand containing two nitrogen and two oxygen donor groups where n=1 or 2.

In accordance with still another aspect of this invention, a catalytic method for dealkylation of a phosphate ester bond containing compound comprises reacting the phosphate ester bond containing compound with an active agent selected from a group of compounds consisting of

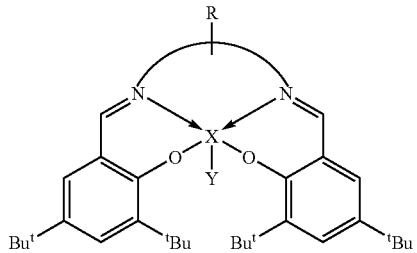

wherein R=alkyl, aryl or alkylaryl, X=a group 13 element other than boron and Y=a potential counteranion in the presence of $BBr_3$.

Alternatively, the catalytic method of dealkylation of a phosphate ester bond containing compound may be defined as comprising reacting the phosphate ester bond containing compound with an active agent selected from a group of compounds consisting of

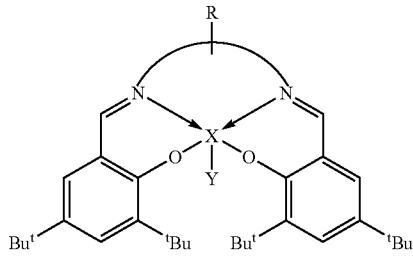

wherein R=—$(CH_2)_2$—, —$(CH_2)_3$— and a phenyl group, X=aluminum, gallium, indium or thallium and Y=a halide, a chlorate or a nitrate in the presence of $BBr_3$.

In accordance with still another alternative, a method of cleaving a phosphate ester bond may be described as comprising reacting a phosphate ester bond containing compound with an active agent selected from a group of compounds consisting of a general formula $(LX)_nY$ wherein X is selected from a group consisting of aluminum, gallium, indium and thallium; Y is selected from a group consisting of a halide, a chlorate, a sulfate and a nitrate; and L is a chelating ligand containing two nitrogen and two oxygen donor groups (where n=1 or 2) in the presence of $BBr_3$.

DETAILED DESCRIPTION OF THE INVENTION

A new class of compounds has been developed that can serve as stoichiometric or catalytic reagents for the breaking of phosphate ester bonds. The compounds can be written as the general formula $(LX)_nY$ where X is selected from a group consisting of aluminum, gallium, indium and thallium, Y is selected from a group consisting of a halide, a chlorate, a sulfate and a nitrate and L is a chelating ligand containing two nitrogen and two oxygen donor groups where n=1 or 2.

More specifically, the compounds may be described as having the structural formula

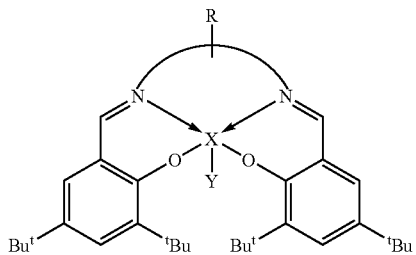

wherein R=alkyl, aryl or alkylaryl, X=a group 13 element other than boron and Y=a counteranion. Typically, where R=alkyl, the alkyl has between 2 and 8 carbon atoms. Still more specifically describing the invention, R=—(CH$_2$)$_2$—, —(CH$_2$)$_3$— and a phenyl group, X=aluminum, gallium, indium or thallium and Y=a halide, a chlorate or a nitrate. Particularly useful embodiments of the compounds of the present invention include but are not limited to:

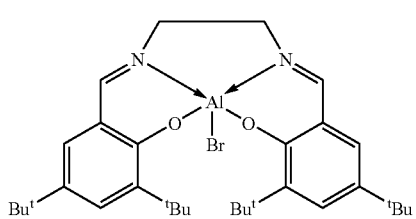

salen($^t$Bu)AlBr

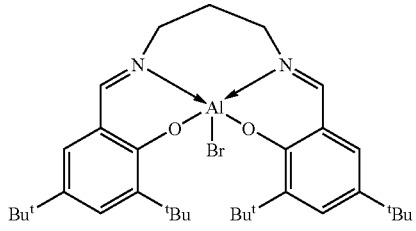

salpen($^t$Bu)AlBr

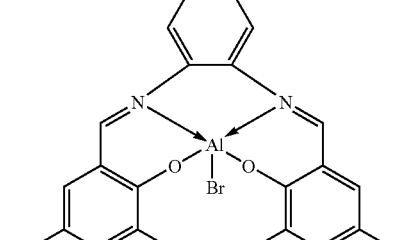

salophen($^t$Bu)AlBr

In the compounds, one group 13 element capable of five-coordinate geometry is bound by a ligand containing two nitrogen and two oxygen donor groups and a counteranion. When combined with a molecule containing a phosphate ester bond (—P—O—C—) the compounds undergo dissociation of one of the counteranion which then attacks the carbon atom of the phosphate ester bond (—O—C—). The cleaved phosphate can be removed by addition of boron bromide. This also regenerates the original compounds and thereby renders the process catalytic.

The breaking of a phosphate ester bond is a critical step in the destruction of nerve agents such as

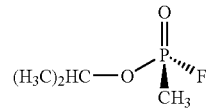

Sarin

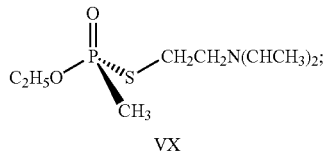

VX and pesticides and insecticides such as

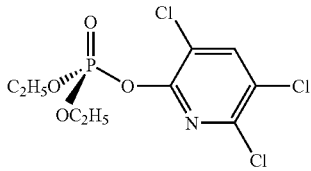

chloropyrifos

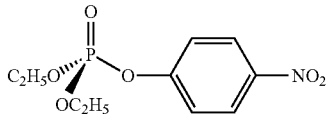

paraoxon

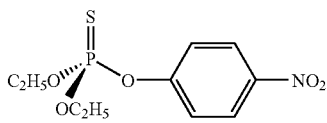

parathion

Such an approach is also useful in destroying other biologically active agents or organic reagents incorporating a phosphate ester bond.

The compounds of the present invention are relatively easily prepared by the redistribution of (a) (C$_2$H$_5$)$_3$X wherein X=aluminum, gallium, indium or thallium and (b) XY$_3$ where X=aluminum, gallium, indium, or thallium and Y=a counteranion such as a halide, a chlorate, a sulfate or a nitrate in toluene to produce in situ (C$_2$H$_5$)$_2$XY. A solution of R($^t$Bu)H$_2$, where R=alkyl, aryl or alkylaryl (e.g. salen($^t$Bu)H$_2$, salpen($^t$Bu)H$_2$ and salophen($^t$Bu)H$_2$), in toluene is then transferred to the reaction mixture. The reaction mixture is then refluxed and filtered and dried to produce the compounds of the present invention.

Compound (LX)$_n$Y, where Y=chlorate, sulfate or nitrate, may be prepared by stirring (LX)$_n$Y, where Y=a halide, with NaClO$_3$, Na$_2$SO$_4$ or NaNO$_3$ respectively.

In addition to the novel compounds described above, the present invention also relates to novel compositions comprising those novel compounds in a compatible solvent. Compatible solvents include but are not limited to chloroform, toluene, methylene chloride, tetrahydrofuran and mixtures thereof.

Still further, the present invention relates to a method for cleaving a phosphate ester bond. That method comprises reacting a phosphate ester bond containing compound with an active agent selected from the compounds or compositions of the present invention.

Further, a catalytic method for dealkylation of a phosphate ester bond comprises reacting a phosphate ester bond containing compound with an active agent selected from a compound or composition of the present invention in the presence of boron bromide ($BBr_3$).

The following syntheses and examples are presented to further illustrate the invention, but the invention is not to be considered as limited thereto. In the examples, all air-sensitive manipulations were conducted using standard bench-top Schlenk line technique in conjunction with an inert atmosphere glove box. All solvents were rigorously dried prior to use. All glassware was cleaned with a base and an acid wash and dried in an oven at 130° C. overnight prior to use. The ligands salen($^t$Bu)$H_2$, salpen($^t$Bu)$H_2$ and salophen($^t$Bu)$H_2$) were synthesized according to the literature procedure (see, for example, L. Deng, E. N. Jacobsen, *J. Org. Chem.* 1992, 57, 4320) All other starting materials were obtained from Sigma Aldrich. NMR data were obtained on Varian Gemini-200 and Varian VXR-400 instruments. Chemical shifts were reported relative to SiMe$_4$ for $^1$H and $^{13}$C and AlCl$_3$ in $D_2O$ for $^{27}$Al and are reported in ppm. Infrared transmission spectra were recorded at room temperature using the potassium bromide pellet technique on a Fourier-transform Magna-IR ESP 560 spectrometer.

EXAMPLE 1

Synthesis of salen($^t$Bu)AlBr

To a rapidly stirred solution of Et$_2$AlBr in toluene, prepared in situ by the redistribution of triethyl aluminum (0.42 g, 3.60 mmol) and aluminum(III) bromide (1M solution in, dibromomethane 1.8 mL, 1.80 mmol), a solution of salen ($^t$Bu)$H_2$ (2.69 g, 5.46 mmol) in toluene was cannula transferred. The reaction mixture was refluxed for 8 hours and filtered. The volatiles were removed under vacuum from the clear yellow filtrate to give a yellow microcrystalline solid which was purified by recrystallization from toluene. Single crystals suitable for X-ray analysis were grown from slow diffusion of hexane vapor into a concentrated CH$_2$Cl$_2$ solution of salen($^t$Bu)AlBr. Yield: 2.69 g (73.8%). Mp: 330–332° C. (dec.). $^1$H NMR (CDCl$_3$): δ 1.33 (s, 18H, C(CH$_3$)$_3$), 1.57 (s, 18H, C(CH$_3$)$_3$), 3.97 (m, 4H, NCH$_2$), 7.08 (d, 2H, PhH), 7.60 (d, 2H, PhH), 8.40 (s, 2H, N=CH); $^{13}$C NMR (CDCl$_3$): δ 29.7 C(CH$_3$)$_3$), 31.3 (C(CH$_3$)$_3$), 34.0 (CCH$_3$)$_3$), 35.5 (CCH$_3$)$_3$), 54.5 (NCH$_2$), 118.2 (Ph), 127.3 (Ph), 131.6 (Ph), 139.1 (Ph), 141.3 (Ph), 162.7 (Ph), 170.4 (NCH); $^{27}$Al NMR (CDCl$_3$): δ 38 (W$_{1/2}$=5183 Hz). IR v/cm$^{-1}$: 2962 m, 2905 w, 2866 w, 1648 s, 1628 s, 1544 m, 1475 m, 1444 m, 1421 w, 1390 w, 1361 w, 1310 w, 1257 w, 1180 w, 867 w, 845 m, 816 w, 786 w, 756 w, 608 m, 586 w. MS (EI, positive): 597 (M$^+$, 8%), 517 M$^+$—Br, 100%), 501 (M$^+$—Br—O, 44%).

EXAMPLE 2

Synthesis of salpen($^t$Bu)AlBr

To a rapidly stirred solution of Et$_2$AlBr in toluene, prepared in situ by the redistribution of triethyl aluminum (0.24 g, 2.08 mmol) and aluminum(III) bromide (1M solution in, dibromomethane 1.0 mL, 1.00 mmol), a solution of salpen ($^t$Bu)H$_2$ (1.57 g, 3.10 mmol) in toluene was cannula transferred. The reaction mixture was refluxed for 17 hours. The cloudy yellow solution was concentrated under vacuum to about one third of its volume. The yellow precipitate was isolated by cannula filtration, washed with ~15 mL of hexane, dried under vacuum and recrystallized from toluene. X-ray quality crystals were grown from slow diffusion of hexane vapor into a concentrated CH$_2$Cl$_2$ solution of salpen ($^t$Bu)AlBr. Yield: 1.04 g (55%). Mp: 333–334° C. (dec.). $^1$H NMR (CDCl$_3$): δ 1.30 (s, 18H, C(CH$_3$)$_3$), 1.50 (s, 18H, C(CH$_3$)$_3$), 2.23 (m, 2H, CH$_2$CH$_2$CH$_2$), 3.85 (m, 4H, NCH$_2$), 7.07 (d, 2H, Ph—H), 7.56 (d, 2H, Ph—H), 8.29 (s, 2H, N=CH); $^{13}$C NMR (CDCl$_3$): δ 27.2 (CH$_2$), 29.7 (C(CH$_3$)$_3$), 31.3 (C(CH$_3$)$_3$), 33.9 (CCH$_3$)$_3$), 35.4 (CCH$_3$)$_3$), 55.1 (NCH$_2$), 118.1 (Ph), 127.2 (Ph), 131.4 (Ph), 138.9 (Ph), 141.0 (Ph), 162.5 (Ph), 172.0 (N=CH); $^{27}$Al NMR (CDCl$_3$): δ 36 (W$_{1/2}$=3339 Hz). IR v/cm$^{-1}$: 2956 m, 2906 w, 2866 w, 1642 s, 1624 s, 1548 m, 1463 s, 1418 m, 1390 w, 1361 m, 1312 m, 1259 m, 1180 m, 1097 w, 863 m, 847 m, 784 w, 755 w, 601 m. MS (EI, positive): 531 (M$^+$—Br, 100%).

EXAMPLE 3

Synthesis of salophen($^t$Bu)AlBr

To a rapidly stirred solution of Et$_2$AlBr in toluene, prepared in situ by the redistribution of triethyl aluminum (0.21 g, 1.08 mmol) and aluminum(III) bromide (1M solution in dibromomethane, 0.90 mL, 0.90 mmol), a solution of salophen($^t$Bu)H$_2$ (1.46 g, 2.70 mmol) in toluene was cannula transferred. The golden yellow solution was refluxed for 15 hours. Then it was concentrated under vacuum to about one third of its volume. Yellow crystals precipitated after cooling at −30° C. for 24 hours. The crystals were isolated by cannula filtration, washed with hexane and dried under vacuum. Yield: 1.54 g (88%). Mp: 320° C. (dec.). $^1$H NMR (CDCl$_3$): δ 1.37 (s, 18H, C(CH$_3$)$_3$), 1.63 (s, 18H, C(CH$_3$)$_3$), 7.24 (d, 2H, Ph—H), 7.35 (m, 2H, Ph—H), 7.66 (m, 2H, Ph—H), 7.71 (d, 2H, Ph—H), 8.94 (s, 2H, N=CH); $^{13}$C NMR (CDCl$_3$): δ 29.8 (C(CH$_3$)$_3$), 31.2 (C(CH$_3$)$_3$), 34.1 (C(CH$_3$)$_3$), 35.6 (C(CH$_3$)$_3$), 115.4 (Ph), 115.7 (Ph), 118.5 (Ph), 126.7 (Ph), 127.5 (Ph), 128.2 (Ph), 129.1 (Ph), 133.2 (Ph), 137.5 (Ph), 139.8 (Ph), 141.6 (Ph), 161.2 (Ph), 162.4 (Ph), 164.1 (N=CH); $^{27}$Al NMR (CDCl$_3$): δ 32 (W$_{1/2}$=5183 Hz). IR (KBR) v/cm$^{-1}$: 2961 s, 2905 w, 2868 w, 1621 s, 1554 m, 1542 s, 1469 s, 1474 m, 1445 m, 1420 m, 1391 wm, 1361 s, 1311 m, 1255 m, 1202 w, 1179 w, 865 w, 847 m, 786 w, 757 w, 610 m. MS (EI, positive): 646 (M$^+$, 13%), 565 (M$^+$—Br, 95%), 549 (M$^+$—Br—O, 100%).

EXAMPLE 4

Dealkylation

A.) Salen($^t$Bu)AlBr

In a vial 30 mg (0.05 mmol) salen(t)AlBr was dissolved in about 1 mL CDCl$_3$. The solution was transferred to a NMR tube in which trimethyl phosphate (1.96 µL, 0.017 mmol, density 1.197 g/mL) was added with a syringe. The mixture was shaken and monitored by $^1$H NMR. The % dealkylation was calculated from the peak integrations of methyl bromide produced and unchanged phosphate.

B.) Salpen($^t$Bu)AlBr

In a vial 30 mg (0.05 mmol) salpen(t)AlBr was dissolved in about 1 mL CDCl$_3$. The solution was transferred to a NMR tube in which trimethyl phosphate (1.91 µL, 0.016 mmol, density 1.197 g/mL) was added with a syringe. The mixture was shaken and monitored by $^1$H NMR. The % dealkylation was calculated from the peak integrations of methyl bromide produced and unchanged phosphate.

C.) Salophen($^t$Bu)AlBr

In a vial 30 mg (0.05 mmol) salophen(t)AlBr was dissolved in about 1 mL CDCl$_3$. The solution was transferred to a NMR tube in which trimethyl phosphate (1.81 µL, 0.015 mmol, density 1.197 g/mL) was added with a syringe. The mixture was shaken and monitored by $^1$H NMR. The % dealkylation was calculated from the peak integrations of methyl bromide produced and unchanged phosphate.

TABLE 1

% Dealkylation[a] of trimethyl phosphate (TMP) and tributyl phosphate (TBP) with Salen($^t$Bu)AlBr compounds.

| Compound | Salen ($^t$Bu)AlBr | | Salpen ($^t$Bu)AlBr | | Salophen ($^t$Bu)AlBr | |
| --- | --- | --- | --- | --- | --- | --- |
|  | TMP | TBP | TMP | TBP | TMP | TBP |
| 30 minutes | 64 | 12 | 35 | 7 | 18 | 100 |
| 2 hours | 79 | 100 | 44 | 100 | 30 | 100 |
| 4 hours | 89 | 100 | 44 | 100 | 40 | 100 |
| 6 hours | 91 |  | 56 |  | 46 |  |
| 8 hours | 93 |  | 58 |  | 58 |  |
| 10 hours | 95 |  | 62 |  | 64 |  |
| 12 hours | 96 |  | 67 |  | 69 |  |
| 24 hours | 96 | 100 | 69 | 100 | 85 | 100 |

[a]Calculated from the integration of $^1$H NMR spectra of methyl bromide produced and unchanged trimethyl phosphate at room temperature in CDCl$_3$. In CD$_3$OD after 24 hours salen($^t$Bu)AlBr showed no dealkylation while salpen($^t$Bu)AlBr and salophen($^t$Bu)AlBr had 4% and 3% dealkylation of TMP, respectively.

EXAMPLE 5

Catalytic Dealkylation

A.) Salen($^t$Bu)AlBr

In a vial 15 mg (0.025 mmol) salen(t)AlBr was dissolved in about 1 mL CDCl$_3$. The solution was transferred to a NMR tube in which trimethyl phosphate (29.30 µL, 0.25 mmol, density 1.197 g/mL) and boron tribromide (0.25 mL, 0.25 mmol, 1M solution in hexane) were added with a syringe. The mixture was shaken and monitored by $^1$H NMR. The % dealkylation was calculated from the peak integrations of methyl bromide produced and unchanged phosphate.

B.) Salpen($^t$Bu)AlBr

In a vial 15 mg (0.025 mmol) salpen(t)AlBr was dissolved in about 1 mL CDCl$_3$. The solution was transferred to a NMR tube in which trimethyl phosphate (28.65 µL, 0.25 mmol, density 1.197 g/mL) and boron tribromide (0.25 mL, 0.25 mmol, 1M solution in hexane) were added with a syringe. The mixture was shaken and monitored by $^1$H NMR. The % dealkylation was calculated from the peak integrations of methyl bromide produced and unchanged phosphate.

C.) Salophen($^t$Bu)AlBr

In a vial 15 mg (0.023 mmol) salophen(t)AlBr was dissolved in about 1 mL CDCl$_3$. The solution was transferred to a NMR tube in which trimethyl phosphate (27.15 µL, 0.23 mmol, density 1.197 g/mL) and boron tribromide (0.23 mL, 0.23 mmol, 1M solution in hexane) were added with a syringe. The mixture was shaken and monitored by $^1$H NMR. The % dealkylation was calculated from the peak integrations of methyl bromide produced and unchanged phosphate.

D.) Control: BBr$_3$

In an NMR tube containing about 1 mL CDCl$_3$, trimethyl phosphate (29.30 µL, 0.25 mmol, density 1.197 g/mL) and boron tribromide (0.25 mL, 0.25 mmol, 1M solution in hexane) were added with a syringe. The mixture was shaken and monitored by $^1$H NMR. The % dealkylation was calculated from the peak integrations of methyl bromide produced and unchanged phosphate.

TABLE 2

Catalytic dealkylation of trimethyl phosphate (TMP) with Salen($^t$Bu)AlBr compounds. Numbers represent % dealkylation.[a]

| Compound | 1 + TMP + BBr$_3$ (1:10:10) | 2 + TMP + BBr$_3$ (1:10:10) | 3 + TMP + BBr$_3$ (1:10:10) | TMP + BBr$_3$ (1:1) |
| --- | --- | --- | --- | --- |
| 30 minutes | 88 | 78 | 82 | 58 |
| 2 hours | 100 | 92 | 84 | 67 |
| 6 hours | 100 | 100 | 95 | 67 |
| 24 hours | 100 | 100 | 95 | 81 |

[a]Calculated from the integration of $^1$H NMR spectra of methyl bromide produced and unchanged trimethyl phosphate at room temperature in CDCl$_3$. 1 = salen($^t$Bu)AlBr, 2 = salpen($^t$Bu)AlBr, 3 = salophen($^t$Bu)AlBr.

EXAMPLE 6

Synthesis of Salen Aluminum Nitrate

The product of Example 1 is subjected to an anion exchange reaction. Specifically, salen($^t$Bu)AlBr is stirred with sodium nitrate in 1:1 ratio in ethanol to produce salen($^t$Bu)AlNO$_3$.

EXAMPLE 7

Synthesis of Salpen Aluminum Sulfate

The product of Example 2 is subjected to an anion exchange reaction. Specifically, salpen($^t$Bu)AlBr is stirred with sodium sulfate in 2:1 ratio in ethanol to produce (salpen($^t$Bu)Al)$_2$SO$_4$.

EXAMPLE 8

Synthesis of Salophen Aluminum Chlorate

The product of Example 3 is subjected to an anion exchange reaction. Specifically, salophen($^t$Bu)AlBr is stirred with sodium chlorate in 1:1 ratio in ethanol to produce salophen($^t$Bu)AlClO$_3$.

EXAMPLE 9

Preparation of Gallium, Indium and Thallium Compounds of the Present Invention Gallium, indium or thallium are substituted for aluminum in the starting materials of examples 1, 2 or 3.

EXAMPLE 10

Preparation of Salen($^t$Bu)AlCl and Salophen($^t$Bu)AlCl

These compounds are prepared by alkane elimination between the Salen($^t$Bu)H$_2$ or Salophen($^t$Bu)H$_2$ ligand and dialkylaluminum chloride.

The foregoing description of a preferred embodiment of the present invention has been presented for purposes of illustration and description. It is not intended to be exhaustive or to limit the invention to the precise form disclosed. Obvious modifications or variations are possible in light of the above teachings.

The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims and their fair and broad interpretation in any way.

What is claimed is:

1. A method of cleaving a phosphate ester bond, comprising:

reacting a phosphate ester bond containing compound with an active agent selected from a group of compounds consisting of

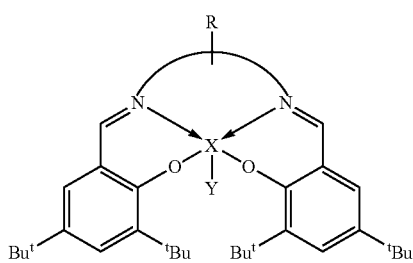

wherein R=alkyl, aryl or alkylaryl, X=a group 13 element other than boron and Y=a counteranion.

2. A method of cleaving a phosphate ester bond, comprising:

reacting a phosphate ester bond containing compound with an active agent selected from a group of compounds consisting of

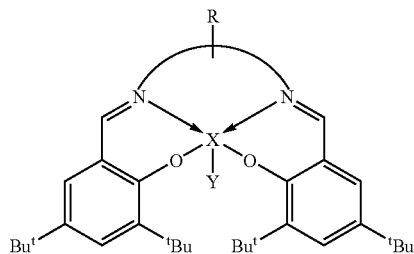

wherein R=—(CH$_2$)$_2$—, —(CH$_2$)$_3$— and a phenyl group, X=aluminum, gallium, indium or thallium and Y=a halide, a chlorate or a nitrate.

3. A catalytic method for dealkylation of a phosphate ester bond containing compound, comprising reacting said phosphate ester bond containing compound with an active agent selected from a group of compounds consisting of

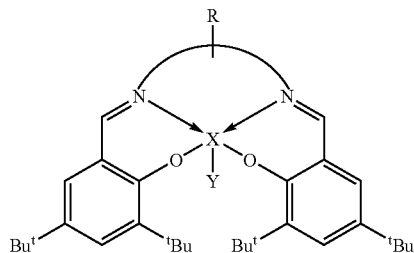

wherein R=alkyl, aryl or alkylaryl, X=a group 13 element other than boron and Y=a counteranion in the presence of BBr$_3$.

4. A catalytic method for dealkylation of a phosphate ester bond containing compound, comprising reacting said phosphate ester bond containing compound with an active agent selected from a group of compounds consisting of

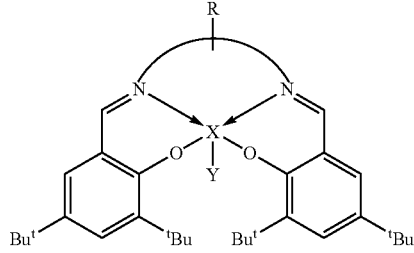

wherein R=—(CH$_2$)$_2$—, —(CH$_2$)$_3$— and a phenyl group, X=aluminum, gallium, indium or thallium and Y=a halide, a chlorate or a nitrate in the presence of BBr$_3$.

5. A method for cleaving a phosphate ester bond, comprising:

reacting a phosphate ester bond containing compound with an active agent selected from a group of compounds consisting of a general formula (LX)$_n$Y wherein:

X is selected from a group consisting of aluminum, gallium, indium and thallium;

Y is selected from a group consisting of a halide, a chlorate, a sulfate and a nitrate; and L is a chelating ligand containing two nitrogen and two oxygen donor groups, where n=1 or 2.

6. The method of claim 5 further including adding BBr$_3$.

* * * * *